United States Patent [19]
Chan

[11] Patent Number: 5,698,556
[45] Date of Patent: Dec. 16, 1997

[54] METHOTREXATE ANALOGS AND METHODS OF USING SAME

[76] Inventor: Carey L. Chan, 4113 Sano St., Los Angeles, Calif. 90065

[21] Appl. No.: 485,645

[22] Filed: Jun. 7, 1995

[51] Int. Cl.$^6$ .................................. A61K 31/505
[52] U.S. Cl. .......................... 514/249; 544/260
[58] Field of Search .................. 544/409, 260, 544/258; 514/249

[56] References Cited

U.S. PATENT DOCUMENTS

| | | | |
|---|---|---|---|
| 2,512,572 | 6/1950 | Smith et al. | 544/260 |
| 3,098,069 | 7/1963 | Camerino | 544/409 |
| 3,158,612 | 11/1964 | Bernardi | 544/409 |
| 3,328,402 | 6/1967 | Winter | 544/409 |
| 3,487,082 | 12/1969 | Cragoe et al. | 544/409 |

(List continued on next page.)

FOREIGN PATENT DOCUMENTS

| 6-73026 | 3/1994 | Japan | 544/409 |
|---|---|---|---|

OTHER PUBLICATIONS

Rosowsky et al., *Biochemical Pharmacology*, 40, 851 (1990).
Taylor et al., *Journal of Am. Chem. Soc.*, 95, 6413 (1973).
Tomita et al., poster presentation at NIH Centennial MRRS–MARC Symposium (Oct. 1–3, 1987).
Chan et al., poster presentation at the *Society for Advancement of Chicanos and Native Americans in Science* (SACNAS) meeting held in Los Angeles, California (Sep. 25–26, 1986).
Chaykovsky et al., *J. Med. Chem.*, 18, 909 (1975).
Chaykovsky et al., *Journal of Med Chem.*, 17, 1212 (1974).
Chaykovsky, *J. Org. Chem.*, 402, (1), 145 (1975).
Frei III et al., *Clin. Pharmacol. Exp. Ther.*, 6, 160 (1965).
Furst et al., *Journal of Pharmaceutical Sciences*, 79(9), 782 (1990).
Goldman et al., *Pharmac. Ther.*, 28, 77 (1985).
Goldman, *Annals New York Academy of Science*, 186, 400 (1971).
Goldman, *Biochem. Biophys. Acta*, 233, 624 (1971).
Henkin et al., *J. Med. Chem.*, 26, 1193 (1983).
Kempton et al., *J. Med. Chem.*, 25, 475 (1982).

(List continued on next page.)

*Primary Examiner*—Donald G. Daus
*Attorney, Agent, or Firm*—Leydig, Voit & Mayer, Ltd.

[57] ABSTRACT

The present invention provides methotrexate analogs having the formula:

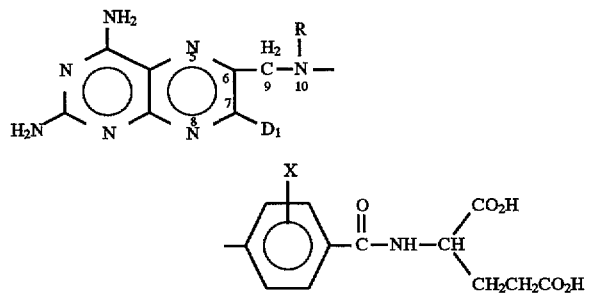

wherein R is methyl or hydro, X is halo or hydro, and $D_1$ is —$NR_1R_2$ wherein either both $R_1$ and $R_2$ are hydrogen, or one is hydrogen and the other is $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, $C_1$–$C_5$ alkyl phenyl, C(=O)R' wherein R' is hydrogen, $C_1$–$C_5$ alkyl, phenyl, or $C_1$–$C_5$ alkyl phenyl, C(=O)OR" wherein R" is hydrogen, $C_1$–$C_5$ alkyl, phenyl, or $C_1$–$C_5$ alkyl phenyl, amino, C(=NH)$NH_2$, C(=O)$NH_2$, or C(=S)$NH_2$, and structurally related derivatives, as well as pharmaceutical compositions comprising such MTX analogs, methods of synthesis of the MTX analogs, and use of the MTX analogs in modulating cellular functions, or in treating cancer and other diseases or disorders capable of being treated using MTX.

14 Claims, 3 Drawing Sheets

U.S. PATENT DOCUMENTS

| | | | |
|---|---|---|---|
| 3,879,394 | 4/1975 | Donald | 544/409 |
| 3,892,801 | 7/1975 | Kazan . | |
| 3,981,983 | 9/1976 | Caston et al. . | |
| 3,989,703 | 11/1976 | Niculescu-Duvaz | 544/260 |
| 4,043,759 | 8/1977 | Charm et al. . | |
| 4,057,548 | 11/1977 | Wiecko | 544/260 |
| 4,067,867 | 1/1978 | Wiecko | 544/260 |
| 4,079,056 | 3/1978 | Piper et al. | 544/260 |
| 4,080,325 | 3/1978 | Ellard | 544/260 |
| 4,093,607 | 6/1978 | Sela et al. . | |
| 4,102,455 | 7/1978 | Charm et al. . | |
| 4,136,101 | 1/1979 | Kazan . | |
| 4,224,446 | 9/1980 | Catalucci | 544/260 |
| 4,279,992 | 7/1981 | Boguslaski et al. . | |
| 4,306,064 | 12/1981 | Ellard et al. | 544/260 |
| 4,374,987 | 2/1983 | Singh et al. | 544/260 |
| 4,376,767 | 3/1983 | Sloan . | |
| 4,378,428 | 3/1983 | Farina et al. | 435/7 |
| 4,401,592 | 8/1983 | Yoshikumi et al. . | |
| 4,416,882 | 11/1983 | Hartman | 544/409 |
| 4,421,913 | 12/1983 | Ellard et al. | 544/260 |
| 4,489,065 | 12/1984 | Walton et al. | 536/118 |
| 4,622,218 | 11/1986 | Bodor | 514/536 |
| 4,625,014 | 11/1986 | Senter et al. | 530/300 |
| 4,638,045 | 1/1987 | Kohn et al. | 530/323 |
| 4,671,958 | 6/1987 | Rodwell et al. | 530/387 |
| 4,699,784 | 10/1987 | Shih et al. | 530/391 |
| 4,767,859 | 8/1988 | Zimmerman | 544/258 |
| 4,785,080 | 11/1988 | Farina et al. | 530/402 |
| 4,816,395 | 3/1989 | Hancock et al. | 436/800 |
| 4,886,780 | 12/1989 | Faulk | 514/8 |
| 4,918,165 | 4/1990 | Soll et al. | 530/391 |
| 4,925,662 | 5/1990 | Oguchi et al. | 530/391 |
| 4,939,240 | 7/1990 | Chu et al. | 530/387 |
| 4,997,913 | 3/1991 | Hellstrom et al. | 530/389 |
| 5,010,103 | 4/1991 | Kalman | 514/495 |
| 5,028,697 | 7/1991 | Johnson et al. | 530/388 |
| 5,030,719 | 7/1991 | Umemoto et al. | 530/391 |
| 5,057,313 | 10/1991 | Shih et al. | 530/391 |
| 5,059,413 | 10/1991 | Reardan et al. | 530/391 |
| 5,082,928 | 1/1992 | Best | 530/389 |
| 5,084,560 | 1/1992 | Hellstrom et al. | 530/391 |
| 5,106,950 | 4/1992 | Farina et al. | 530/345 |
| 5,108,987 | 4/1992 | Faulk | 514/8 |
| 5,196,533 | 3/1993 | Ayling et al. | 544/258 |
| 5,382,582 | 1/1995 | Chan | 544/260 |

OTHER PUBLICATIONS

Loera et al., poster presentation at 1992 National Conference on Undergraduate Research (Mar. 17, 1992).

Lopez et al., *Biochemical Pharmacology*, 35(16) 2834 (1986).

McGuire et al., *Biochemical Pharmacology*, 42(12), 2400 (1991).

Rosowsky et al., *J. Med. Chem.*, 17, 1308 (1974).

Rosowsky et al., *J. Med. Chem.*, 21, 170 (1978).

Rosowsky et al., *J. Med. Chem.*, 21, 380 (1978).

Chu et al *Cancer Chemotherapy and Biological Response Modifiers Annual 13*, Pinedo et al., eds. (Elsevier Science Publ. B.V., 1992), pp. 1–10, 25–26, 70–74, 119, 138, 140, 144–147.

METHOTREXATE ANALOGS AND METHODS OF USING SAME

STATEMENT AS TO RIGHTS TO INVENTIONS MADE UNDER FEDERALLY SPONSORED RESEARCH AND DEVELOPMENT

This invention was made with government support, Grant No. S06GM08177, awarded by the National Institutes of Health. The government may have certain rights in this invention.

FIELD OF THE INVENTION

The present invention relates to novel methotrexate analogs, pharmaceutical compositions containing the analogs, methods of synthesizing the analogs, and methods for their use. These analogs are useful in modulating cellular functions and in treating diseases or disorders that are capable of being treated using MTX, particularly cancer.

BACKGROUND OF THE INVENTION

Within the cell, important molecules called tetrahydrofolates THF) power the life-sustaining processes of DNA synthesis, replication and repair by coenzymatically providing substrates necessary for these processes. THF are biosynthesized intracellularly through reduction of folic acid or other dihydrofolate intermediates by the enzyme dihydrofolate reductase (DHFR). The pteridine compound, methotrexate (MTX; N-[4-[[(2,4-diamino-6-pteridinyl methyl] methylamino]benzoyl]-L-glutamicacid), is structurally quite similar to folic acid. As a result of this structural similarity, MTX can bind to active sites on DHFR, and, through competitive inhibition, block the formation of THF needed in the biosynthesis of DNA and RNA.

This ability of MTX to inhibit nucleic acid synthesis has been exploited in the treatment of aberrant cell growth. In particular, since many malignant cells proliferate more rapidly than normal cells, and since actively proliferating cells are more sensitive to the effect of MTX, in many cases, MTX can be used to selectively impair cancerous cell growth without damaging normal cell growth. As a result of its effectiveness against rapidly proliferating cells, MTX is one of the most widely used anticancer agents. For example, MTX is employed in the treatment of neoplastic diseases such as gestational choriocarcinoma, chorioadenoma destruens, hydatidiform mole, acute lymphocytic leukemia, breast cancer, epidermoid cancers of the head and neck, advanced mycosis fungoides, lung cancer, and non-Hodgkins lymphomas (*Physicians Desk Reference*, 45th ed., Medical Economical Co., Inc., 1185–89 (Des Moines, Iowa (1991)). Moreover, MTX is an effective immunosuppressive agent, with utility in the prevention of the graft-versus-host reaction that can result from tissue transplants, as well as in the management of inflammatory diseases. Consequently, MTX can be employed in the treatment of severe and disabling psoriasis and rheumatoid arthritis (Hoffmeister, *The American Journal of Medicine*, 30, 69–73 (1983); Jaffe, *Arthritis and Rheumatism*, 31, 299 (1988)).

The numerous patents that have been issued disclosing MTX and MTX analogs, methods of synthesizing MTX or analogs thereof, and uses for MTX attest to the significance of MTX in treatment of aberrant cell growth. For example, U.S. Pat. No. 2,512,572 covers the active agent MTX, and U.S. Pat. Nos. 3,892,801, 3,989,703, 4,057,548, 4,067,867, 4,079,056, 4,080,325, 4,136,101, 4,224,446, 4,306,064, 4,374,987, 4,421,913, and 4,767,859 claim methods for preparing MTX or potential intermediates in the synthesis of MTX. Other patents disclose labelled analogs of MTX, such as U.S. Pat. Nos. 3,981,983, 4,043,759, 4,093,607, 4,279, 992, 4,376,767, 4,401,592, 4,489,065, 4,622,218, 4,625,014, 4,638,045, 4,671,958, 4,699,784, 4,785,080, 4,816,395, 4,886,780, 4,918,165, 4,925,662, 4,939,240, 4,983,586, 4,997,913, 5,024,998, 5,028,697, 5,030,719, 5,057,313, 5,059,413, 5,082,928, 5,106,950, and 5,108,987, wherein MTX is bound to a radionucleotide or fluorescent label, amino acid, polypeptide, transferrin or ceruloplasmin, chondroitin or chondroitin sulfate, antibody, or binding partner for a specific cell-surface receptor of target cells for use in assays of MTX, in timed-release of MTX, as toxins selective for cancer cells, or to facilitate transport of MTX across membranes or in vivo barriers. Of the numerous patents issued disclosing methods of using MTX, a variety of patents such as U.S. Pat. Nos. 4,106,488, 4,558,690, and 4,662,359 disclose methods of using MTX to treat cancer. Additionally, U.S. Pat. Nos. 4,396,601 and 4,497,796 describe the use of MTX to select cells that have been transfected with vectors containing a DHFR selectable marker, and U.S. Pat. No. 5,043,270 discloses the use of MTX to select for or assess gene amplification events. The basis for these two latter approaches is that an increase in the number of copies of the DHFR gene within a cell correspondingly increases resistance to MTX.

Despite the broad utility and utilization of MTX, treatment with this agent involves a strong risk to the patient. Since MTX interferes with cell replication and division, actively proliferating non-malignant tissues such as bone marrow and intestinal mucosa are more sensitive to MTX and may demonstrate impaired growth due to treatment. More importantly, MTX is associated with renal and hepatic toxicity when applied in the "high dose regimen" that is typically required for maximum efficiency (Barak et al., *J. American Coll. Nutr.*, 3, 93–96 (1984)). It appears that a major metabolite of MTX, 7-OH-MTX, is the source of this toxicity. In both man and monkeys, MTX is converted in vivo to 7-hydroxymethotrexate (7-OH-MTX) (Borsi et al., *Cancer Chemother. Pharmacol.*, 27, 164–67 (1990); Jacobs et al. *J. Clin. Investig.*, 57, 534–38, (1976)). Also, 7-OH-MTX has been found in both urine and plasma samples of patients following high dose MTX therapy (Watson et al., *Cancer Res.*, 43, 4648 (1983); Breithaupt et al., *Cancer Treatment Rep.*, 9, 1733 (1982); Heiko et al., *Pharmacol.*, 26, 138–143 (1990); Chatelut et al., *J. Pharmaceutical Sci.*, 80, 730–34 (1991); Lopez et al., *Biochemical Pharmacol.*, 35, 2834–36 (1986)).

To alleviate MTX-induced toxicity, high dose MTX therapy can be administered in conjunction with citrovorum factor as a "rescue" agent for normal cells (Christenson et al., *J. Clin. Oncol.*, 6, 797–801 (1988)). While citrovorum factor rescue reduces MTX toxicity to non-malignant cells, it does not solve the problem of renal and hepatic impairment due to the formation of 7-OH-MTX.

Because of the undisputed value of MTX in therapy and research, attempts have been made to increase the effectiveness of MTX and decrease the problems attendant with its use. Many investigators have modified the structure of MTX in attempts to synthesize more potent MTX derivatives. The most effective derivatives include aminopterin, which possesses a hydrogen instead of a methyl group at position N-10, and 4-amino derivatives with halogen substitution on the para-aminobenzoic moiety, such as dichloromethotrexate (Frei et al., *Clin. Pharmacol. and Therap.*, 6, 160–71 (1965)). Additional MTX derivatives have been synthesized by: (i) preparing ester derivatives of the glutamyl moiety, (ii)

replacing the glutamic acid with amino acids and peptides, (iii) adding a methyl group at the 7-position, (iv) poly-(L-lysine) conjugation, and (v) substituting the gamma amides (Rosowsky and Yu, *J. Med. Chem.*, 21, 170–75 (1978); Rosowsky et al., *J. Med. Chem.*, 21, 380–86 (1978); Chaykovsky et al., *J. Med. Chem.*, 18, 909–12 (1975); Rosowsky and Chen, *J. Med. Chem.*, 17, 1308–11 (1974)). More recent modification attempts include the synthesis of lysine and ornithine derivatives of MTX (Kempton et al., *J. Med Chem.*, 25, 475–477 (1982); Patil et al., *J. Med. Chem.*, 32, 1559–65 (1989)). These attempts to improve the efficacy of MTX have not yet proven entirely successful. Whereas some of the MTX derivatives, such as 7-methyl substituted MTX (Rosowsky and Chen, *J. Med. Chem.*, 17, 1308–11 (1974)), demonstrate impaired antifolate antagonism, others, such as 3',5'-difluoro MTX, demonstrate little or no increase in biological activity as compared with MTX (Tomcuf, *J. Organic Chem.*, 26, 3351 (1961)). Still other derivatives, like the 2' and 3' monofluorinated derivatives of aminopterin, appear promising, but animal studies remain to be performed (Henkin and Washtien, *J. Med. Chem.*, 26, 1193–1196 (1983)). Similarly, 7,8-dihydro-8-methyl-MTX has been prepared, but the biological properties of this and other compounds remain to be fully investigated (Chaykovsky, *J. Org. Chem.*, 40 (1), 145–146 (1975)).

Consequently, there remains a need for MTX derivatives having improved or at least equivalent efficacy as MTX and having reduced toxicity for normal cells. One study investigated the influence of lipophilicity and carboxyl group content on the ability of MTX derivatives to undergo 7-hydroxylation in vitro (Rosowsky et al., *Biochem. Pharmacol.*, 40, 851–857 (1990)). While increasing lipophilicity was found to facilitate hydroxylation, the addition of two to five poly-glutamyl residues to the MTX molecule caused a decrease in the rate of hydroxylation at the 7-position. However, this study did not determine the effectiveness of the glutamylated derivatives at inhibiting DHFR. Thus, it is an object of the present invention to provide MTX derivatives that are at least similar to MTX in ability to inhibit DHFR and that demonstrate reduced hydroxylation at the C-7 position.

In particular, it is an object of the present invention to provide novel analogs of MTX which modulate at least one cellular function, such as DHFR-mediation of DNA synthesis or repair, and show reduced hydroxylation at the 7-position, as compared with MTX. It is an additional object of the present invention to provide pharmaceutical compositions comprising therapeutically acceptable excipients and novel analogs of MTX. It is a further object of the present invention to provide methods of synthesizing such novel analogs of MTX. Yet another object of the present invention is to provide methods of using the novel analogs of MTX to modulate at least one cellular function, and in treating diseases or disorders that are capable of being treated using MTX, particularly cancer.

These and other objects and advantages of the present invention, as well as additional inventive features, will be apparent from the description of the invention provided herein.

BRIEF SUMMARY OF THE INVENTION

The present invention provides certain methotrexate analogs, pharmaceutical compositions containing the analogs, methods of synthesizing the analogs, and methods for their use.

In particular, this invention provides methotrexate analogs of the formula:

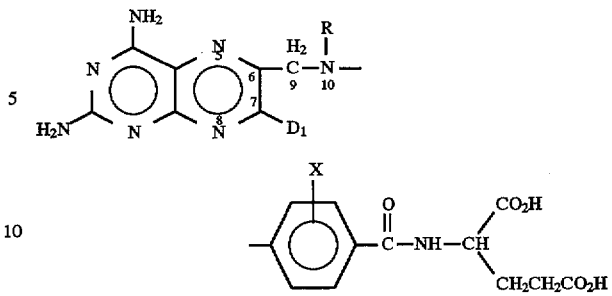

wherein R is methyl or hydro, X is halo or hydro, and $D_1$ is $-NR_1R_2$ wherein either both $R_1$ and $R_2$ are hydrogen, or one is hydrogen and the other is $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, $C_1$–$C_5$ alkyl phenyl, C(=O)R' wherein R' is hydrogen, $C_1$–$C_5$ alkyl, phenyl, or $C_1$–$C_5$ alkyl phenyl, C(=O)OR" wherein R" is hydrogen, $C_1$–$C_5$ alkyl, phenyl, or $C_1$–$C_5$ alkyl phenyl, amino, C(=NH)$NH_2$, C(=O)$NH_2$, or C(=S)$NH_2$, and structurally related derivatives, as well as pharmaceutical compositions comprising such MTX analogs, and method of synthesizing such MTX analogs. These analogs are useful in the modulation of cellular function in much the same manner as MTX, and in treating diseases or disorders that are capable of being treated using MTX, particularly cancer, yet exhibit reduced 7-hydroxylation as compared to MTX.

DETAILED DESCRIPTION OF THE PREFERRED EMBODIMENTS

Figure 1A:
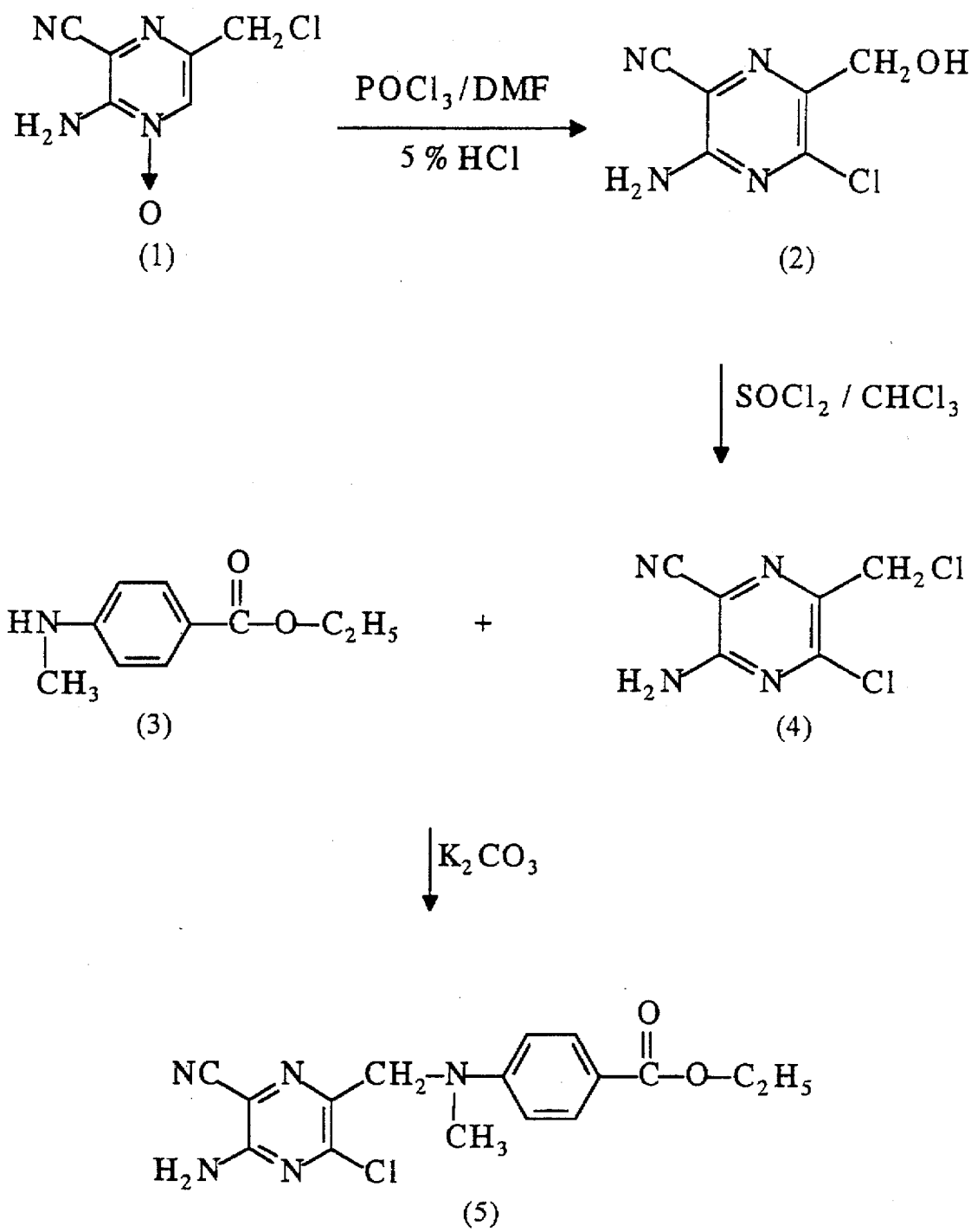
FIG. 1A depicts a portion of the schematic of a synthetic route to the preparation of the 7-$NR_1R_2$-MTX analogs of the present invention.

The present invention provides certain novel methotrexate analogs, pharmaceutical compositions containing the analogs, methods of synthesizing the analogs, and methods for their use.

The present invention provides MTX analogs capable of functioning as effective folate antagonists and having potentially reduced renal and hepatic toxicity as compared with MTX. These novel analogs have been developed based on the premise that since formation of the toxic metabolite 7-OH-MTX occurs through hydroxylation of the 7-position of MTX, inhibition of oxidation at this position can be employed to decrease or block the formation of 7-OH-MTX. Inhibition of oxidation in the context of the present invention appears to be accomplished by increasing the strength of the bond between C-7 and its substituent. The present inventive compounds reduce oxidation at the 7-position by replacing the hydrogen at C-7 with an atom or group that binds more tightly and that will decrease the oxidation at the 7-position as compared to unmodified methotrexate. The MTX analogs contemplated in the context of the present invention have antifolate activity that is comparable to that of MTX, and can replace MTX in its applications, thus reducing renal and hepatic toxicity while maintaining desired efficacy.

The methotrexate analogs of the present invention have the general structure indicated below:

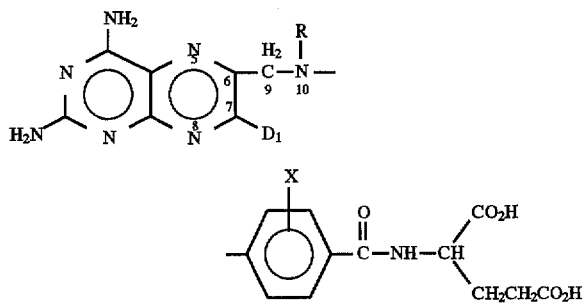

wherein R is methyl or hydro, X is halo or hydro, and $D_1$ is $-NR_1R_2$, wherein either both $R_1$ and $R_2$ are hydrogen, or one is hydrogen and the other is $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, $C_1$–$C_5$ alkyl phenyl, C(=O)R' wherein R' is hydrogen, $C_1$–$C_5$ alkyl, phenyl, or $C_1$–$C_5$ alkyl phenyl, C(=O)OR" wherein R" is hydrogen, $C_1$–$C_5$ alkyl, phenyl, or $C_1$–$C_5$ alkyl phenyl, amino, $C(=NH)NH_2$, $C(=O)NH_2$, or $C(=S)NH_2$, as well as therapeutically acceptable analogs, derivatives, and salts thereof. When X is halo, one or more X can be present on the benzene ring, and the location of X can be at the 2, 3, 4, and 5 positions, and combinations thereof.

The methotrexate analogs of the present invention include the salts made from any suitable organic or inorganic acids, and organic or inorganic bases. Examples of suitable acids include hydrochloric acid, nitric acid, sulfuric acid, phosphoric acid, carbonic acid, amino acids such as glycine, lysine, and serine, acetic acid, citric acid, oxalic acid, phthalic acid, and the like. Examples of suitable bases include sodium hydroxide, potassium hydroxide, ammonium hydroxide, potassium carbonate, sodium carbonate, quaternary ammonium hydroxide, calcium hydroxide, aluminum hydroxide, and the like.

A preferred methotrexate analog utilized in the context of the present invention is 7-$NH_2$-MTX, which is a compound of the aforesaid structure wherein R is methyl, $D_1$ is $-NR_1R_2$ wherein both $R_1$ and $R_2$ are hydrogen, and X is hydrogen. Also preferred are methotrexate analogs wherein $D_1$ is $-NR_1R_2$ wherein either $R_1$ or $R_2$ is hydrogen, and the other is $C_1$–$C_5$ alkyl, and X is halo or hydrogen, and more preferred are methotrexate analogs wherein $D_1$ is $-NR_1R_2$ wherein either $R_1$ or $R_2$ is hydrogen, and the other is methyl or ethyl, and X is halo or hydrogen. Other preferred compounds are methotrexate analogs wherein $D_1$ is $-NR_1R_2$ wherein either $R_1$ or $R_2$ is hydrogen, and the other is $C_1$–$C_5$ alkyl, and X is hydrogen, and other more preferred are methotrexate analogs wherein $D_1$ is $-NR_1R_2$ wherein either $R_1$ or $R_2$ is hydrogen, and the other is methyl or ethyl, and X is hydrogen. Still other preferred methotrexate analogs are similar to these preferred analogs but wherein R is hydrogen, such as is found in the folate antagonist aminopterin, instead of the methyl group that is present at this position in MTX. Additionally, since long chain polyglutamyl derivatives of MTX enhance intracellular retention of the drug and are also inhibitory to other folate requiring enzymes (U.S. Pat. No. 5,010,103), the present novel analogs may be polyglutamylated.

The MTX analogs of the present invention may be used alone or in association with other suitable compounds and carriers, and also may be used in combination with other active agents. The present invention, therefore, also includes pharmaceutical compositions comprising pharmaceutically active excipients and an active agent, where the active agent is an analog of MTX modified to reduce hydroxylation at the C-7 carbon. In particular, the present invention contemplates as active agents in such pharmaceutical compositions 7-$NR_1R_2$-MTX, wherein either both $R_1$ and $R_2$ are hydrogen, or one is hydrogen and the other is $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, $C_1$–$C_5$alkyl phenyl, C(=O)R' wherein R' is hydrogen, $C_1$–$C_5$ alkyl, phenyl, or $C_1$–$C_5$ alkyl phenyl, C(=O)OR" wherein R" is hydrogen, $C_1$–$C_5$ alkyl, phenyl, or $C_1$–$C_5$ alkyl phenyl, amino, $C(=NH)NH_2$, $C(=O)NH_2$, or $C(=S)NH_2$, and therapeutically acceptable derivatives and salts of these active agents. The present invention contemplates as more preferred active agents in such pharmaceutical compositions 7-$NR_1R_2$-MTX, wherein either both $R_1$ and $R_2$ are hydrogen, or one is hydrogen and the other is methyl or ethyl. The active agent may be present in the pharmaceutical composition in any suitable quantity. The pharmaceutically acceptable excipients include, for example, any suitable vehicles, adjuvants, carriers or diluents, and are readily available to the public. The pharmaceutical compositions of the present invention may further contain other active agents as are well known in the art.

The present invention provides methods of synthesizing the MTX analogs of the present invention, particularly the preferred analogs 7-$NR_1R_2$-MTX, wherein either both $R_1$ and $R_2$ are hydrogen, or one is hydrogen and the other is $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, $C_1$–$C_5$ alkyl phenyl, C(=O)R' wherein R' is hydrogen, $C_1$–$C_5$ alkyl, phenyl, or $C_1$–$C_5$ alkyl phenyl, C(=O)OR" wherein R" is hydrogen, $C_1$–$C_5$ alkyl, phenyl, or $C_1$–$C_5$ alkyl phenyl, amino, $C(=NH)NH_2$, $C(=O)NH_2$, or $C(=S)NH_2$, and structurally related derivatives.

The MTX analogs of the present invention may be produced by any suitable method. For instance, alkyl-4-[N-(2,4-diamino-7-halo-6-pteridinylmethyl)-N-methylamino]-benzoic derivative such as the benzoic ester or amide, wherein the alkyl is any suitable alkyl group including $C_1$–$C_{10}$ alkyl, and the 7-halo substituent is fluoro, chloro, bromo, or iodo, can be reacted under suitable conditions with ammonia to produce the alkyl-4-[N-(2,4,7-triamino-6-pteridinylmethyl)-N-methylamino]-benzoic derivative, or with a primary amine to produce the alkyl-4-[N-(2,4-diamino-7-alkylamino-6-pteridinylmethyl)-N-methylamino]-benzoic derivative. The benzoic ester derivative is a preferred derivative. The benzoic ester or amide prepared as above can be hydrolyzed by suitable means, such as by heating with a suitable aqueous acid or alkali, to obtain 4-[N-(2,4,7-triamino-6-pteridinylmethyl)-N-methylamino]-benzoic acid, or 4-[N-(2,4-diamino-7-alkylamino-6-pteridinylmethyl)-N-methylamino]-benzoic acid.

The alkyl-4-[N-(2,4-diamino-7-halo-6-pteridinylmethyl)-N-methylamino]-benzoic derivative can be prepared by any suitable method. A preferred method of producing the MTX analogs of the present invention involves the use of 3-amino-6-(halomethyl)-2-pyrazinecarbonitrile-4-oxide as the starting material. The halogen of the halomethyl group can be fluorine, chlorine, bromine, or iodine, with chlorine being a preferred halogen. The starting material is converted by suitable means to the alkyl-4-[N-(2,4-diamino-7-halo-6-pteridinylmethyl)-N-methylamino]-benzoic derivative, wherein the alkyl may be any suitable alkyl group including $C_1$–$C_{10}$ alkyl, and the 7-halo substituent can be fluoro, chloro, bromo, or iodo, with chloro being a preferred halo substituent.

The aforedescribed 3-amino-6-(halomethyl)-2-pyrazinecarbonitrile-4-oxide starting material may be reduced first at the amine oxide to the corresponding pyrazine carbonitrile, namely, 3-amino-6-(halomethyl)-2-pyrazinecarbonitrile, and the latter can then be halogenated by any known halogenating agent to halogenate at the 5-position of the pyrazine ring. Examples of reducing agents to reduce the pyrazine oxide to pyrazine include triphenylphosphine, lithium aluminum hydride, hydrogen and nickel, phosphorous trichloride, triethyl phosphite, carbon disulfide, and sulfur. Examples of suitable halogenating agents to halogenate at the 5-position of the pyrazine ring include elemental halogens, halogens in presence of iron or copper catalysts such as $FeCl_3$ or $CuCl_2$, hypohalous acid, iodine monochloride, and the like.

In a preferred method, the aforesaid starting material is first reacted with a phosphorous oxyhalide, such as phosphorous oxychloride. Any suitable solvent may be used to carry out the reaction. Examples of suitable solvents include N,N-dimethylformamide (DMF), N-methylpyrrolidinone (NMP), and the like. The reaction can be carried out at a suitable temperature, preferably at a temperature in the range of from about 30° C. to about 85° C. The resulting product is then heated with an aqueous acid such as hydrochloric acid to obtain the 3-amino-5-halo-6-(hydroxymethyl)-2-pyrazinecarbonitrile.

The 3-amino-5-halo-6-(hydroxymethyl)-2-pyrazinecarbonitrile can be reacted with a suitable halogenating agent to convert the hydroxymethyl group to the halomethyl group. Examples of suitable halogenating agents include hydrogen acids such as hydrogen chloride, hydrogen bromide, and the like, thionyl halide such as thionyl chloride, thionyl bromide, and the like, phosphorous pentahalide such as phosphorous pentachloride, and phosphorous trihalide such as phosphorous trichloride. Thionyl chloride is a preferred halogenating agent.

The 3-amino-5-halo-6-(halomethyl)-2-pyrazinecarbonitrile can be converted to the 4-[N-(2,4-diamino-7-halo-6-pteridinylmethyl)-N-methylamino]-benzoic derivative by any suitable method. For instance, the 3-amino-5-halo-6-(halomethyl)-2-pyrazinecarbonitrile can be first reacted with ethyl-4-methylaminobenzoate to produce ethyl-4-[N-(2-amino-3-cyano-6-halo-5-pyrazinylmethyl)-N-methylamino]benzoate. In the above reaction, the halogen of the halomethyl group is substituted by the methylamino group of the benzoate. The reaction can be carried out in a suitable reaction medium comprising a solvent such as DMF, NMP, acetonitrile, tetrahydrofuran, dioxalan, dioxane, diethyl ether, glycol dimethyl ether, glycol diethyl ether, diethylene glycol diethyl ether, chloroform, and the like. Tetrahydrofuran is a preferred solvent. The reaction is carried out at a temperature in the range of from about 25° C. to about 125° C., and preferably at a temperature in the range of from about 30° C. to about 70° C. Excessively higher temperatures are to be avoided in view of possible unwanted side reactions such as reaction at the 5-halo position. The reaction is preferably carrried out in the presence of a base to act as a scavenger for the hydrogen halide acid produced as a byproduct during the reaction. Any suitable base, such as an organic or inorganic base, can be used. Examples of suitable organic bases include pyridine, triethylamine, N,N-dimethylaminopyridine, and the like. Examples of suitable inorganic bases include sodium, potassium or calcium carbonate or bicarbonate, and sodium or potassium hydroxide. Potassium carbonate is a preferred inorganic base.

The ethyl-4-[N-(2-amino-3-cyano-6-halo-5-pyrazinylmethyl)-N-methylamino]benzoate can then be reacted with guanidine hydrochloride in the presence of a suitable base to produce 4-[N-(2,4-diamino-7-halo-6-pteridinylmethyl)-N-methylamino]benzoate. Examples of suitable bases include alkoxides such as metal alkoxides. Examples of suitable metal alkoxides include alkoxides of alkali and alkaline earth metals and aluminum, such as sodium methoxide, sodium ethoxide, sodium propoxide, sodium butoxide, potassium propoxide, calcium ethoxide, calcium propoxide, aluminum isopropoxide, and the like. Sodium isopropoxide is a preferred alkoxide. The alkoxide can be generated in situ by dissolving the metal in the alcohol. Thus, for instance, sodium metal can be dissolved in isopropanol, and the guanidine hydrochloride and the ethyl-4-[N-(2-amino-3-cyano-6-halo-5-pyrazinylmethyl)-N-methylamino]benzoate can be mixed thereinto. The reaction can be carried out using any suitable solvent as the medium for the reaction. A preferred solvent is an alcohol, with isopropanol being more preferred. The reaction is carried out at a temperature in the range of from about 25° C. to about 100° C., and preferably in the range of from about 60° C. to about 80° C., and more preferably at the reflux temperature of the solvent.

To prepare compounds having one or more halogen atoms on the benzene ring of the benzoate, the benzene ring of the ethyl-4-methylaminobenzoate or 4-methylaminobenzamide can be substituted by one or more halogen atoms. The position of substitution on the benzene ring can be at the 2, 3, 5, and 6-positions, and combinations thereof. Examples of halogenated benzoic ester or amide include ethyl-4-methylamino-3-chloro-benzoate, 4-methylamino-3-chloro-benzamide, ethyl-4-methylamino-2-chloro-benzoate, methylamino-2-chloro-benzamide, ethyl-4-methylamino-3,5-dichloro-benzoate, 4-methylamino-3,5-dichloro-benzamide, ethyl-4-methylamino-2,6-dichloro-benzoate, and methylamino-2,6-dichloro-benzamide. The aforesaid halogenated benzoic ester or amide can be prepared by any suitable method. For instance, 4-methylaminobenzoic ester or amide can be halogenated at the 3 and 5 positions by common halogenation methods known to those of ordinary skill in the art, including reacting with a halogen in the presence of a suitable catalyst such as an iron or copper catalyst.

The ethyl-4-[N-(2,4-diamino-7-halo-6-pteridinylmethyl)-N-methylamino]-benzoic derivative can be converted to ethyl-4-[N-/2,4,7-triamino-6-pteridinylmethyl)-N-methylamino]benzoate by any suitable method. A preferred method is by reaction with ammonia, more preferably with ammonia gas. The reaction is carried out by heating the above 7-halo compound in a suitable solvent saturated with ammonia gas. Examples of suitable solvents include DMF, dimethylsulfoxide (DMSO), NMP, and the like, with DMSO being preferred. The ethyl ester can be suitably hydrolyzed to obtain the free carboxylic acid. A suitable acid or base can be used to effect the hydrolysis. If a base is used, the salt of the carboxylic acid can be converted to the acid form by further treatment with an acid.

In a similar manner, the ethyl-4-[N-(2,4-diamino-7-halo-6-pteridinylmethyl)-N-methylamino]-benzoic derivative can be converted to ethyl-4-[N-(2,4-diamino-7-methylamino-6-pteridinylmethyl)-N-methylamino]benzoate by reacting the 7-halo derivative with methylamine, preferably with methylamine gas. The 7-methylamino ester obtained can be converted to the acid form as described above.

The 4-[N-(2,4,7-triamino-6-pteridinylmethyl)-N-methylamino]benzoic acid or 4-[N-(2,4-diamino-7-methylamino-6-pteridinylmethyl)-N-methylamino]benzoic acid can be coupled with diethylglutamate to obtain the diethyl 4,7-diamino-N-10-methylpteroylglutamate or the diethyl 4-amino-7-methylamino-N-10-methylpteroylglutamate, using suitable methods, for instance, by heating them together in a suitable solvent such as DMF, NMP, or DMSO, and preferably in the presence of a suitable coupling agent. Examples of suitable coupling agents include N,N'-carbonyldiimidazole, dicyclohexylcarbodiimide, phosphorous oxychloride, titanium tetrachloride, and others known to those of ordinary skill in the art. A preferred coupling agent is a combination of triethylamine and ethyl cyanophosphate. Any suitable combination of triethylamine and ethyl cyanophosphonate can be employed, preferably an equimolar combination. The coupling reaction is carried out, preferably by first mixing for a short time, preferably for about 1 to 10 minutes, the 4-[N-(2,4,7-triamino-6-pteridinylmethyl)-N-methylamino] benzoic acid or 4-[N-(2,4-diamino-7-methylamino-6-pteridinylmethyl)-N-methylamino]benzoic acid with the coupling agent, preferably in a suitable solvent such as DMF, NMP, or DMSO, at a suitable temperature, preferably in the range of from about 25° C. to about 100° C., and more preferably in the range of from about 70° C. to about 90° C. The mixture is then cooled, preferably to about 25° C., and diethyl glutamate hydrochloride and triethylamine are added and stirred, preferably at about 25° C. for a suitable period of time, preferably for about 40 to 60 hours. The resulting methotrexate derivative can be isolated and purified by conventional methods known to those of ordinary skill in the art.

Figure 1B:
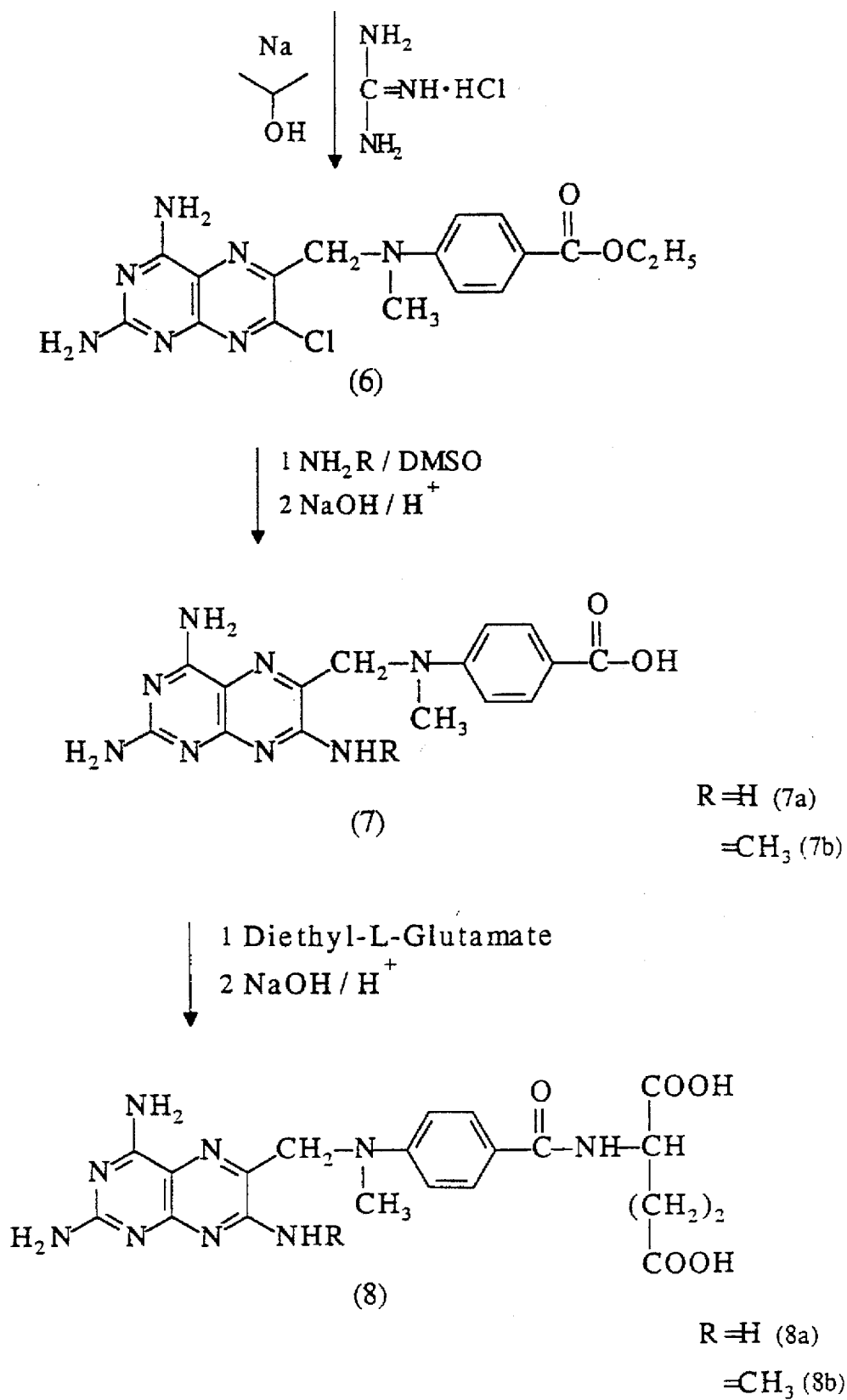
FIG. 1B depicts the remaining portion of the schematic of the synthetic route depicted in FIG. 1A.

A suitable method of synthesizing 7-$NR_1R_2$-MTX wherein either both $R_1$ and $R_2$ are hydrogen, or one is hydrogen and the other is $C_1$–$C_5$ alkyl, is outlined in FIGS. 1A and 1B. A suitable method of synthesizing 7-$NR_1R_2$-MTX wherein both $R_1$ and $R_2$ are hydrogen comprises (a) reacting phosphorus oxychloride with 3-amino-6-(chloromethyl)-2-pyrazinecarbonitrile 4-oxide (1) to yield 3-amino-5-chloro-6-(hydroxymethyl)-2-pyrazinecarbonitrile (2); (b) reacting 3-amino-5-chloro-6-(hydroxymethyl)-2-pyrazinecarbonitrile with thionyl chloride to form 3-amino-5-chloro-6-(chloromethyl)-2-pyrazinecarbonitrile (4); (c) reacting 3-amino-5-chloro-6-(chloromethyl)-2-pyrazinecarbonitrile with ethyl 4-methylaminobenzoate (3) to form ethyl 4-[N-(2-amino-3-cyano-6-chloro-5-pyrazinylmethyl)-N-methylamino] benzoate (5); (d) reacting ethyl 4-[N-(2-amino-3-cyano-6-chloro-5-pyrazinylmethyl)-N-methylamino]benzoate with guanidine to form 4-[N-(2,4-diamino-7-chloro-6-pteridinylmethyl)-N-methylamino]benzoate (6); (e) reacting 4-[N-(2,4-diamino-7-chloro-6-pteridinylmethyl)-N-methylamino]benzoate with ammonia to form 4-[N-(2,4,7-triamino-6-pteridinylmethyl)-N-methylamino]benzoic acid (7a); and (f) coupling 4-[N-(2,4,7-triamino-6-pteridinylmethyl)-N-methylamino]benzoic acid and diethyl L-glutamate hydrochloride.

The method of synthesizing 7-$NR_1R_2$-MTX wherein either $R_1$ or $R_2$ is hydrogen, and the other is $C_1$–$C_5$ alkyl, is also outlined in FIGS. 1A and 1B. This method comprises (a) reacting phosphorus oxychloride with 3-amino-6-(chloromethyl)-2-pyrazinecarbonitrile 4-oxide (1) to yield 3-amino-5-chloro-6-(hydroxymethyl)-2-pyrazinecarbonitrile (2); (b) reacting 3-amino-5-chloro-6-(hydroxymethyl)-2-pyrazinecarbonitrile with thionyl chloride to form 3-amino-5-chloro-6-(chloromethyl)-2-pyrazinecarbonitrile (4); (c) reacting 3-amino-5-chloro-6-(chloromethyl)-2-pyrazinecarbonitrile with ethyl 4-methylaminobenzoate (3) to form ethyl 4-[N-(2-amino-3-cyano-6-chloro-5-pyrazinylmethyl)-N-methylamino] benzoate (5); (d) reacting ethyl 4-[N-(2-amino-3-cyano-6-chloro-5-pyrazinylmethyl)-N-methylamino]benzoate with guanidine to form 4-[N-(2,4-diamino-7-chloro-6-pteridinylmethyl)-N-methylamino]benzoate (6); (e) reacting 4-[N-(2,4-diamino-7-chloro-6-pteridinylmethyl)-N-methylamino]benzoate with methylamine to form 4-[N-(2,4-diamino-7-methylamino-y-pteridinylmethyl)-N-methylamino]benzoic acid (7b); and (f) coupling 4-[N-(2,4-diamino-7-methylamino-y-pteridinylmethyl)-N-methylamino]benzoic acid and diethyl L-glutamate to form the diethyl ester of 7-methylamino-MTX.

All the other steps in the reaction scheme are carried out as described, with routine modifications that would be apparent to the ordinary skilled artisan to improve yield or purity of the isolated 7-substituted MTX derivative.

The methods set forth above can be suitably modified to synthesize other 7-$NR_1R_2$-MTX derivatives, such as the 7-$R_1R_2$-MTX derivatives, wherein either $R_1$ or $R_2$ is hydrogen, and the other is $C_2$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, $C_1$–$C_5$ alkyl phenyl, C(=O)R' wherein R' is hydrogen, $C_1$–$C_5$ alkyl, phenyl, or $C_1$–$C_5$ alkyl phenyl, C(=O)OR" wherein R" is hydrogen, $C_1$–$C_5$ alkyl, phenyl, $C_1$–$C_5$ alkyl phenyl, amino, C(=NH)$NH_2$, C(=O)$NH_2$, or C(=S)$NH_2$.

This can be accomplished by any suitable modification of the above procedures, for instance, by reacting 4-[N-(2,4-diamino-7-chloro-6-pteridinylmethyl)-N-methylamino] benzoate with $NH_2R$, where R is a $C_2$–$C_5$ alkyl, phenyl, $C_1$–$C_5$ alkyl phenyl, C(=O)R' wherein R' is hydrogen, $C_1$–$C_5$ alkyl, phenyl, or $C_1$–$C_5$ alkyl phenyl, or C(=O)OR" wherein R" is hydrogen, $C_1$–$C_5$ alkyl, phenyl, or $C_1$–$C_5$ alkyl phenyl. Thus, for instance, 4-[N-(2,4-diamino-7-chloro-6-pteridinylmethyl)-N-methylamino]benzoate can be reacted with ethylamine, aniline, or toluidine, to obtain, respectively, 4-[N-(2,4-diamino-7-ethylamino-6-pteridinylmethyl)-N-methylamino]benzoate, 4-[N-(2,4-diamino-7-anilino-6-pteridinylmethyl)-N-methylamino] benzoate, or 4-[N-(2,4-diamino-7-toluidino-6-pteridinylmethyl)-N-methylamino]benzoate.

Furthermore, 7-$R_1R_2$-MTX derivatives wherein either $R_1$ or $R_2$ is hydrogen, and the other is C(=O)R' wherein R' is hydrogen, $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, or $C_1$–$C_5$ alkyl phenyl, can be prepared by suitable modifications known to those of ordinary skill in the art, such as by reaction with an acid halide or an acid anhydride. For instance, a 7-$NR_1R_2$-MTX derivative wherein $R_1$ and $R_2$ are hydrogen can be prepared as described above, and the amino group at the 7-position can be reacted with an acid halide having a suitable substituent such as hydrogen, $C_1$–$C_5$ alkyl, $C_1$–$C_5$ haloalkyl, cyano $C_1$–$C_5$ alkyl, $C_1$–$C_5$ hydroxyalkyl, alkoxyalkyl wherein the alkoxy and the alkyl have 1–5 carbon atoms, carboxy $C_1$–$C_5$ alkyl, phenyl, or $C_1$–$C_5$ alkyl phenyl, to obtain 7-$NR_1R_2$-MTX derivatives wherein one of $R_1$ and $R_2$ is hydrogen, and the other is C(=O)R' wherein R' is hydrogen, $C_1$-$C_5$ alkyl, $C_1$-$C_5$ haloalkyl, cyano $C_1$-$C_5$ alkyl, $C_1$-$C_5$ hydroxyalkyl, alkoxyalkyl wherein the alkoxy and the alkyl have 1–5 carbon atoms, carboxy $C_1$-$C_5$ alkyl, phenyl, or $C_1$-$C_5$ alkyl phenyl. The amino groups at the 2- and 4-positions of the pteridine should be suitably protected prior to the reaction with the acid halide. Any suitable protecting group known to those of ordinary skill in the art can be used. For instance, phenacylsulfonyl chloride can be used to protect the amino groups at the 2- and 4- positions. After the reaction with the acid halide or the acid anhydride, the protecting group can be removed by any suitable means, for instance, by zinc and acetic acid.

In addition, 7-$NR_1R_2$-MTX derivatives wherein either $R_1$ or $R_2$ is hydrogen, and the other is C(=O)OR" wherein R" is hydrogen, $C_1$-$C_5$ alkyl, phenyl, or $C_1$-$C_5$ alkyl phenyl can be prepared using suitable modifications. For instance, 7-$R_1R_2$-MTX derivative wherein $R_1$ and $R_2$ are hydrogen can be prepared as described above, and the primary amino group at the 7-position is converted to the isocyanate group by reaction with chloroform by the standard carbylamine reaction in the presence of a base. The resulting isocyanate can be reacted suitably with an alcohol such as methanol, ethanol, propanol, and the like, a phenol, or an alkyl phenol to obtain 7-$NR_1R_2$-MTX derivatives wherein one of $R_1$ and $R_2$ is hydrogen and the other is C(=O)OR" wherein R" is $C_1$-$C_5$ alkyl, phenyl, or $C_1$-$C_5$ alkyl phenyl. As described earlier, suitable methods of protecting the amino groups at the 2- and 4-positions can be employed. Any of the aforesaid 7-$NR_1R_2$-MTX derivatives wherein one of $R_1$ and $R_2$ is hydrogen and the other is C(=O)OR" wherein R" is alkyl may be suitably hydrolyzed to obtain 7-$NR_1R_2$-MTX derivatives wherein one of $R_1$ and $R_2$ is hydrogen and the other is C(=O)OH.

The 7-$NR_1R_2$-MTX derivatives of the present invention wherein either $R_1$ or $R_2$ is hydrogen, and the other is amino, C(=NH)$NH_2$, C(=O)$NH_2$, or C(=S)$NH_2$, can also be prepared by using suitable modifications. For instance, the methotrexate analog of the present invention having one of $R_1$ and $R_2$ as hydrogen and the other as amino or C(=NH)$NH_2$ can be prepared as follows. The 7-halo methotrexate derivative prepared as described above can be reacted with hydrazine or guanidine. Thus, 4-[N-(2,4-diamino-7-chloro-6-pteridinylmethyl)-N-methylamino]benzoate can be suitably reacted with hydrazine or guanidine to obtain, respectively, 4-[N-(2,4-diamino-7-hydrazino-6-pteridinylmethyl)-N-methylamino]benzoate or 4-[N-(2,4-diamino-7-guanidino-6-pteridinylmethyl)-N-methylamino] benzoate. The methotrexate analogs of the present invention having one of $R_1$ and $R_2$ as hydrogen and the other as C(=O)$NH_2$ or C(=S)$NH_2$ can be prepared, for instance, by reacting the 7-amino analog with urea or thiourea. The amino groups at the 2- and 4- positions can be protected by suitable protecting groups, for instance, as described earlier. Thus, the amino groups of 4-[N-(2,4,diamino-7-halo-6-pteridinylmethyl)-N-methylamino]benzoate can be suitably protected, and the halo group substituted by an amino group by reaction with, for instance, ammonia. The above analog can be suitably reacted with urea or thiourea, and the protected amino groups deprotected as described earlier, to obtain respectively, methotrexate analogs having one of $R_1$ and $R_2$ as hydrogen and the other as C(=O)$NH_2$ or C(=S)$NH_2$. The reaction is carried out by any suitable means, preferably in an acidic environment and at elevated temperatures, preferably in the range of from about 80° to about 100° C.

Thus, the present invention provides a method of synthesizing a methotrexate analog having the formula:

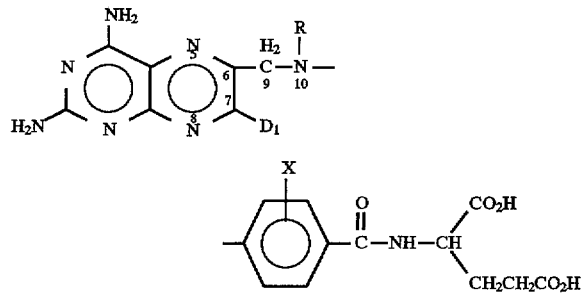

wherein R is methyl or hydro, X is halo or hydro, and $D_1$ is —$NR_1R_2$ wherein either both $R_1$ and $R_2$ are hydrogen, or one of $R_1$ and $R_2$ is hydrogen and the other is $C_1$-$C_5$ alkyl, $C_1$-$C_5$ haloalkyl, cyano $C_1$-$C_5$ alkyl, $C_1$-$C_5$ hydroxyalkyl, alkoxyalkyl wherein the alkoxy and the alkyl have 1–5 carbon atoms, carboxy $C_1$-$C_5$ alkyl, phenyl, $C_1$-$C_5$ alkyl phenyl, C(=O)R' wherein R' is hydrogen, $C_1$-$C_5$ alkyl, phenyl, or $C_1$-$C_5$ alkyl phenyl, C(=O)OR" wherein R" is hydrogen, $C_1$-$C_5$ alkyl, phenyl, or $C_1$-$C_5$ alkyl phenyl, amino, C(=NH)$NH_2$, C(=O)$NH_2$, or C(=S)$NH_2$, said method comprising contacting diethyl L-glutamate and a benzoic acid compound of the formula:

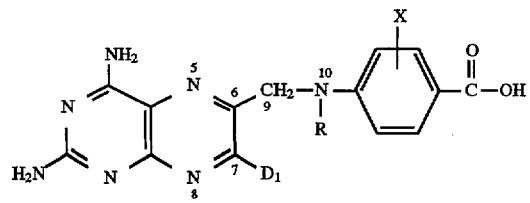

wherein R is methyl or hydro, X is halo or hydro, and $D_1$ is —$NR_1R_2$ wherein either both $R_1$ and $R_2$ are hydrogen, or one of $R_1$ and $R_2$ is hydrogen and the other is $C_1$-$C_5$ alkyl, $C_1$-$C_5$ haloalkyl, cyano $C_1$-$C_5$ alkyl, $C_1$-$C_5$ hydroxyalkyl, alkoxyalkyl wherein the alkoxy and the alkyl have 1–5 carbon atoms, carboxy $C_1$-$C_5$ alkyl, phenyl, $C_1$-$C_5$ alkyl phenyl, C(=O)R' wherein R' is hydrogen, $C_1$-$C_5$ alkyl, phenyl, or $C_1$-$C_5$ alkyl phenyl, C(=O)OR" wherein R" is hydrogen, $C_1$-$C_5$ alkyl, phenyl, or $C_1$-$C_5$ alkyl phenyl, amino, C(=NH)$NH_2$, C(=O)$NH_2$, or C(=S)$NH_2$.

The present invention further includes a method of modulating at least one cellular function, such as DHFR mediation of DNA synthesis or repair, by contacting cells with one of the active agents of the present invention, wherein the active agent is an analog of MTX modified to reduce hydroxylation at the C-7 carbon. In particular, the present inventive method contemplates modulation of a cellular function by the active agents 7-$NR_1R_2$-MTX, wherein either both $R_1$ and $R_2$ are hydrogen, or one is hydrogen and the other is $C_1$-$C_5$ alkyl, $C_1$-$C_5$ haloalkyl, cyano $C_1$-$C_5$ alkyl, $C_1$-$C_5$ hydroxyalkyl, alkoxyalkyl wherein the alkoxy and the alkyl have 1–5 carbon atoms, carboxy $C_1$-$C_5$ alkyl, phenyl, $C_1$-$C_5$ alkyl phenyl, C(=O)R' wherein R' is hydrogen, $C_1$-$C_5$ alkyl, phenyl, or $C_1$-$C_5$ alkyl phenyl, C(=O)OR" wherein R" is hydrogen, $C_1$-$C_5$ alkyl, phenyl, or $C_1$-$C_5$ alkyl phenyl, amino, C(=NH)$NH_2$, C(=O)$NH_2$, or C(=S)$NH_2$, and therapeutically acceptable derivatives and salts of these active agents. In this respect, the present inventive MTX analogs can be used in place of MTX for applications of MTX ranging from use as a rodenticide to selecting for gene amplification events. The MTX analogs can be used in treating diseases or disorders that are capable of being treated using MTX. Use of the MTX analogs of the present invention is of particular utility in, for example, the treatment of diseases and disorders including but not limited to cancer, psoriasis, rheumatoid arthritis, and tissue-graft rejection, as well as in conditions requiring immunosuppressive agents. In these capacities, use of the present inventive MTX analogs will result in a reduced rate of formation of the toxic compound 7-OH-MTX that results from breakdown of MTX, and will thus reduce MTX-mediated toxicity.

As regards these applications, the present inventive method includes the administration to an animal, particularly a human, of a therapeutically effective amount of one or more of the aforementioned MTX analogs as an active agent effective in the competitive inhibition of DHFR, particularly an active agent selected from the group consisting of analogs possessing at the C-7 position $-NR_1R_2$, wherein either both $R_1$ and $R_2$ are hydrogen, or one is hydrogen and the other is $C_1-C_5$ alkyl, phenyl, $C_1-C_5$ alkyl phenyl, $C(=O)R'$ wherein $R'$ is hydrogen, $C_1-C_5$ alkyl, phenyl, or $C_1-C_5$ alkyl phenyl, $C(=O)OR''$ wherein $R''$ is hydrogen, $C_1-C_5$ alkyl, $C_1-C_5$ haloalkyl, cyano $C_1-C_5$ alkyl, $C_1-C_5$ hydroxyalkyl, alkoxyalkyl wherein the alkoxy and the alkyl have 1–5 carbon atoms, carboxy $C_1-C_5$ alkyl, phenyl, or $C_1-C_5$ alkyl phenyl, amino, $C(=NH)NH_2$, $C(=O)NH_2$, or $C(=S)NH_2$, and pharmaceutically acceptable derivatives and salts thereof.

One skilled in the art will appreciate that a variety of suitable methods of administering a compound of the present invention to an animal are available, and, although more than one route can be used to administer a particular compound, a particular route can provide a more immediate and more effective reaction than another route. Pharmaceutically acceptable excipients are also well-known to those who are skilled in the art, and are readily available. The choice of excipient will be determined in part by the particular compound, as well as by the particular method used to administer the composition. Accordingly, there is a wide variety of suitable formulations of the pharmaceutical composition of the present invention. The following methods and excipients are merely exemplary and are in no way limiting. However, pharmaceutically acceptable excipients which do not interfere with the inhibition of DHFR are preferred.

Formulations suitable for oral administration can consist of (a) liquid solutions, such as an effective amount of the compound dissolved in diluents, such as water, saline, or orange juice; (b) capsules, sachets or tablets, each containing a predetermined amount of the active ingredient, as solids or granules; (c) suspensions in an appropriate liquid; and (d) suitable emulsions. Tablet forms can include one or more of lactose, mannitol, corn starch, potato starch, microcrystalline cellulose, acacia, gelatin, colloidal silicon dioxide, croscarmellose sodium, talc, magnesium stearate, stearic acid, and other excipients, colorants, diluents, buffering agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The MTX analogs of the present invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They may also be formulated as pharmaceuticals for non-pressured preparations such as for use in a nebulizer or an atomizer.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The formulations can be presented in unit-dose or multi-dose sealed containers, such as ampules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Formulations suitable for topical administration may be presented as creams, gels, pastes, or foams, containing, in addition to the active ingredient, such carriers as are known in the art to be appropriate.

Additionally, the MTX analogs employed in the present invention may be made into suppositories by mixing with a variety of bases such as emulsifying bases or water-soluble bases. Formulations suitable for vaginal administration may be presented as pessaries, tampons, creams, gels, pastes, foams.

The dose administered to an animal, particularly a human, in the context of the present invention should be sufficient to effect a prophylactic or therapeutic response in the animal over a reasonable time frame. One skilled in the art will recognize that dosage will depend on a variety of factors including the strength of the particular compound employed, the condition of the animal, and the body weight of the animal, as well as the severity of the illness and the stage of the disease. The size of the dose will also be determined by the existence, nature, and extent of any adverse side-effects that might accompany the administration of a particular compound. Suitable doses and dosage regimens can be determined by comparisons to anticancer or immunosuppressive agents that are known to effect the desired growth inhibitory or immunosuppressive response, particularly unmodified methotrexate. The preferred dosage is the amount which results in the inhibition of DHFR, without significant side effects. In proper doses and with suitable administration of certain compounds, the present invention provides for a wide range of intracellular effects, e.g., from partial inhibition to essentially complete inhibition of DHFR. This is especially important in the context of the present invention, as this differential inhibition can potentially be used to discriminate between cancer cells and highly proliferative non-malignant cells.

In the treatment of some individuals with the compounds of the present invention, it may be desirable to use a high dose regimen in conjunction with a rescue agent for non-malignant cells. In such treatment, any agent capable of rescue of non-malignant cells can be employed, such as citrovorum factor, folate derivatives, or leucovorin. Such rescue agents are well known to those of ordinary skill in the art. A rescue agent is preferred which does not interfere with the ability of the present inventive compounds to modulate cellular function.

While the examples provided herein involve the synthesis and use of 7-substituted analogs of MTX, the examples do not exclude additional modifications to MTX, for example, such as replacement of the methyl group present on N-10 in MTX with a hydrogen, as is observed for the MTX analog, aminopterin, or halogen substitution on the para-aminobenzoic moiety. Simple modifications of the procedures described herein, such modifications which are well known to those of ordinary skill in the art, allow modifications to be made at positions in MTX other than the ones described, while maintaining or effecting the 7-substitutions described herein.

The following examples further illustrate the present invention and should not be construed as in any way limiting its scope.

EXAMPLES

The following experimental supplies and instruments were employed in carrying out the experiments which form the examples described herein.

NADPH, dihydrofolic acid, L-amethopterine, and chicken liver DHFR were purchased from Sigma Chemical Co. (St. Louis, Mo.). MTX was either purchased from Sigma or obtained from the National institutes of Health (Chemotherapeutic Agents Repository, c/o ERC BioServices Corporation, 1592-E Rockville Pike, Rockville, Md.). Partially purified DHFR from MTX-resistant *L. casei* was obtained from the New England Enzyme Center (Boston, Mass.). 7-OH-MTX, used as a standard solution, and diethyl-p-methylaminobenzoyl glutamate were synthesized from p-methylaminobenzoic acid according to previously described methods (Fu et al., *J. Org. Chem.*, 30, 1277 (1965)). While 7-OH-MTX has been reported to be collected from the rabbit after high dose MTX treatment, this compound was synthesized to ensure purity and authenticity.

Infrared (IR) spectra were recorded on a Beckman 4250 spectrophotometer. $^1H$ nuclear magnetic resonance spectroscopy was conducted with use of a 90-MHz Varian 360 spectrophotometer. High performance liquid chromatography (HPLC) was carried out with use of a Beckman gradient HPLC system. The chromatographic system consisted of a C-$R_5$A chromatopac, SCL-9a system controller and SIL-9A autoinjector. A Shimadzu LC-9A solvent system and a SPD-9AUV spectrophotometric detector were used unless indicated otherwise. Mass spectra were recorded at the University of California (Riverside, Calif.). Elemental analyses were performed by Galbraith Laboratories, Inc. (Knoxville, Tenn.).

Example 1

This example outlines the method of synthesizing MTX analogs possessing some atom other than hydrogen linked to the C-7 position of MTX in conjunction with other substitutions by presenting the synthesis of 7-$NR_1R_2$-MTX, wherein either both $R_1$ and $R_2$ are hydrogen, or one is hydrogen and the other is $C_1$-$C_5$ alkyl. These syntheses entail multi-step processes which result in the incorporation of a primary or secondary amine group at the 7-position of the molecule. This method of synthesis is outlined in FIGS. 1A and 1B.

Synthesis of 3-amino-5-chloro-6-(hydroxymethyl)-2-pyrazinecarbonitrile

In the first step of this synthesis, phosphorus oxychloride (1.9 ml, 0.02 mole) was slowly added while stirring to a solution of 3-amino-6-(chloromethyl)-2-pyrazinecarbonitrile 4-oxide (1) (3.7 g, 0.02 mole) in 20 ml DMF. The temperature of the mixture was maintained at 0°–3° C. throughout this addition. When the addition was completed, the mixture was stirred at this temperature for an additional 10 minutes. After a yellow precipitate was formed, the mixture was heated to 65° C. for 1 hour. DMF was then removed by vacuum evaporation. The residue was washed with 200 ml of cold water, and was then re-dissolved in 200 ml of a boiling solution of 5% HCl, after which the mixture was immediately filtered. The filtrate was stored in the refrigerator overnight. Formed crystals were collected and washed with water. After drying, the yield of the product, 2, was 2.5 g (68%). The product had a melting point of 210°–212° C. The IR spectrum (KBr) of 3-amino-5-chloro-6-(hydroxymethyl)-2-pyrazinecarbonitrile showed absorptions corresponding to —$NH_2$ at 3365.8 and 3318.8 $cm^{-1}$, —C≡N at 2225.9 $cm^{-1}$, and —C=N— at 1648.7 $cm^{-1}$. The nmr spectrum (DMSO-d6) revealed signals at 7.50 δ (2H,s,$NH_2$), 5.20 δ (1H,t,OH), and 4.40 δ (2H,d,$CH_2$). Elemental analysis confirmed the presence of C, H, N, and Cl in the compound.

Synthesis of 3-amino-5-chloro-6-(chloromethyl)-2-pyrazinecarbonitrile

Compound 2 (3.7 g, 0.02 mole) was suspended in 40 ml of chloroform. To this mixture, 1.8 ml of pyridine and 3.0 ml of thionyl chloride were added slowly while stirring. At the end of this addition, the mixture was stirred for four additional hours at room temperature. The solvent was then removed, and the residue was triturated with 100 ml of cold water. After filtration and washing with cold water, the product (4) was dried in air, yielding 4.0 g (91%) of light yellow solid. The melting point of this solid ranged from 173°–174° C. The IR spectrum (KBr) showed absorptions corresponding to —$NH_2$ at 3201 and 3365.8 $cm^{-1}$, —C≡N at 2237.6, and —C=N— at 1648.7 $cm^{-1}$. The nmr spectrum (DMSO-d6) revealed signals at 7.76 δ (2H, s,$NH_2$) and 4.60 (2H,s,$CH_2C_1$).

Synthesis of ethyl 4-[N-(2-amino-3-cyano-6-chloro-5-pyrazinylmethyl)-N-methylamino]benzoate (5)

Compound 4 (4.04 g, 0.02 mole) and ethyl 4-methylaminobenzoate hydrochloride (3) (4.10 g, 0.02 mole) were dissolved in 200 ml of tetrahydrofuran. The solution was chilled in an ice bath, and to the solution was added slowly a potassium carbonate solution (3.0 g, 0.022 mole in 200 ml water) with stirring. After 24 hours of continuous stirring at room temperature, a yellow precipitate was collected and washed with water. Recrystallization of the product from methanol gave 2.4 g (70% yield) of yellow solid 5. This solid had a melting point of 206°–207° C. The IR spectrum (KBr) showed absorptions corresponding to —$NH_2$ at 3389.9, 3194, and 3264 $cm^{-1}$, —C≡N at 2240 $cm^{-1}$, and —C(=O)O— at 1713 $cm^{-1}$. The nmr spectrum (DMSO-d6) revealed signals at 7.75 δ (2H,b,$NH_2$), 7.70 δ (2H,d,arom), 6.67 δ (2H,d,arom), 4.35 δ (2H, s,$CH_2N$—), 4.21 δ (2H,q,$OCH_2CH_3$), 3.20 δ (3H,s,$NCH_3$), and 1.32 δ (3H,t,$CH_2CH_3$). The FAB mass spectrum showed a molecular ion peak at m/z 345. This peak confirmed that the molecular weight of this compound was 345. Elemental analysis confirmed the presence of C, H, N and Cl in the compound.

Synthesis of ethyl 4-[N-(2,4-diamino-7-chloro-6-pteridinylmethly)-N-methylamino]benzoate (6)

In a 1000 ml round bottom flask, sodium metal (0.12 g, 5.5 mmole) was dissolved in 50 ml of 2-propanol while the solution was warmed gradually. To this basic solution was added a solution of guanidine hydrochloride (5.2 g, 5.5 mmole) and 50 ml of 2-propanol. This solution was stirred for 5 minutes before compound 5 in 600 ml 2-propanol was added. The mixture was refluxed for 30 minutes and then evaporated to dryness. The residue was triturated with water, and a yellow solid was obtained and collected. Recrystallization from DMSO gave 1.7 g of the product, 6, corresponding to an 85% yield. The melting point of this product was 222°–223° C. The IR spectrum (KBr) showed absorptions corresponding to —NH$_2$ at 3400 and 3200 cm$^{-1}$, —C=N— at 1713 cm$^{-1}$, and —C(=O)— at 1689 cm$^{-1}$. The nmr spectrum (DMSO-d6) revealed signals at 7.75 δ (2H,d, arom), 6.84 δ (2H,d,arom), 6.90δ (2H,b,NH$_2$), 4.86 δ (2H, s,CH$_2$N), 4.24 δ (2H,q,OCH$_2$), 3.24 δ (3H,s,NCH$_3$), and 1.28 δ (3H,t,CH$_2$CH$_3$). The FAB mass spectrum showed a molecular ion peak at m/z 387. This peak confirmed that the molecular weight of this compound was 387. Elemental analysis confirmed the presence of C, H and N in the compound.

Synthesis of 4-[N-(2,4,7-triamino-6-pteridinylmethyl)-N-methylamino]benzoic acid (7a)

Compound 6 (1.95 g, 5 mmole) was dissolved in 40 ml DMSO. While the mixture was being stirred, ammonia gas was bubbled into the mixture until saturation was achieved. The reaction mixture was stirred in a closed system for 24 hours at 70° C. At cooling, the crystals formed were filtered, and then washed with methanol. After drying, 1.6 gm, corresponding to a 90% yield, of the ethyl ester of compound 7a was obtained as a yellow solid. The melting point of this solid ester was 265°–267° C. The IR spectrum (KBr) showed absorption signals corresponding to NH$_2$ at 3400–3200 cm$^{-1}$ and —C(=O)O— at 1709 cm$^{-1}$. The nmr spectrum (DMSO-d6) revealed signals at 7.74 δ (2H,d, arom), 6.76 δ (2H,d,arom), 6.94 δ (2H,b,NH$_2$), 6.17 δ (2H,b,NH$_2$), 4.65 δ (2H, s,CH$_2$N), 4.22 e (2H,q,OCH$_2$), 3.18 δ (3H, s,NCH$_3$), and 1.28 δ (3H,t,CH$_2$CH$_3$). The FAB mass spectrum showed a molecular ion peak at m/z 368. This peak confirmed that the molecular weight of this compound was 368. Elemental analysis confirmed the presence of C, H and N in the compound.

The ethyl ester of 7a (3.7 gm, 0.01 mole) was hydrolyzed in NaOH/DMSO solution. After acidifying with glacial acetic acid, 2.2 g of compound 7a was obtained, corresponding to a 65% yield. The melting point of this compound was 279°–281° C. The FAB mass spectrum showed a molecular ion peak at m/z 339. This peak confirmed that the molecular weight of this compound was 339.

Synthesis of 4-[N-(2,4-diamino-7-methylamino-ypteridinylmethlyl)-N-methylamino]benzoic acid (7b)

The procedures described for the synthesis of compound 7a were followed for the synthesis of compound 7b with the exception that methylamine was used instead of ammonia in the reaction with compound 6. Using this approach, 3.1 g, corresponding to a 92% yield, of the ethyl ester of compound 7b was obtained as a light yellow solid. The melting point of this compound was greater than 280° C. The nmr spectrum (DMSO-d6) revealed signals at 7.74 δ (2H,d, arom), 7.2 δ (2H,b,NH$_2$), 6.75 δ (2H,d,arom), 7.10 δ (1H, b,NH), 4.65 δ (2H, s,CH$_2$), 1.20 δ (2H,q,OCH$_2$), 3.10 δ (3H, s,NCH$_3$), 3.05 δ (3H,d,NHCH$_3$), and 1.30 δ (3H, t,CH$_2$CH$_3$). The FAB mass spectrum showed a molecular ion peak at m/z 382. This peak confirmed that the molecular weight of this compound was 382.

Compound 7b was obtained after its ethyl ester was hydrolyzed with NaOH in DMSO producing 3.8 g, corresponding to a 60% yield, as a brown solid. The melting point of this compound was greater than 280° C. The nmr spectrum (DMSO-d6) revealed signals at 7.72 δ (2H,d,arom), 6.73 δ (2H,d,arom), 7.20 δ (2H,b,NH$_2$), 6.14 δ (1H,b,NH), 4.65 δ (2H,s,CH$_2$), 3.13 δ(3H,s,NCH$_3$), and 2.94 δ (3H,d, NHCH$_3$).

Synthesis of 4,7-diamino-N-10-methylpteroylglutamic acid (8a)

Compound 7a (1.02 g, 3.0 mmole) was dissolved in 30 ml of DMF. To this solution were added ethyl cyanophosphonate (1.62 ml, 9 mmole) and triethylamine (1.23 ml, 9.0 mmole). The mixture was heated to 80° C. for 2 minutes. After the mixture had been cooled to room temperature, a solution of diethyl L-glutamate hydrochloride (0.72 gm, 3.0 mmole) in triethylamine (0.42 ml, 3.0 mmole) was added to the mixture which was then stirred at room temperature for 48 hours. At the end of 48 hours, 150 ml of water was added to the mixture which was then extracted several times with chloroform. The organic layers were combined and dried over Na$_2$SO$_4$. The chloroform solution was filtered, and the filtrate was evaporated to dryness. The residue was chromatographed on a silica gel column which was eluted with CHCl$_3$:ethanol (4:1). After the eluent was evaporated, the crude product, diethyl 4,7-diamino-N-10-methylpteroylglutamate was obtained as a yellow solid. Recrystallization from ethanol gave 0.5 g, corresponding to a 40% yield, of diethyl ester of 7-aminomethotrexate. The melting point of this compound was 210°–213° C. The IR spectrum (KBr) showed absorption signals corresponding to NH$_2$ at 3108–3451.2 cm$^{-1}$, aliphatic —CH at 2986.0 cm$^{-1}$, —C(=O)O— at 1727.9 cm$^{-1}$, and —C=N— at 1605.5 cm$^{-1}$. The nmr spectrum (DMSO-d6) revealed signals at 8.30 δ (1H,d,CONH), 7.78 δ (2H,d,arom), 7.18 δ (2H, s,NH$_2$), 6.50–7.0 δ (2H,b,NH$_2$), 6.80 δ (2H,d,arom), 6.60 δ (2H,s,NH$_2$), 4.65 δ (2H,s,CH$_2$N), 4.30 δ (1H,m,NCH—), 4.10 δ (4H,q,COOCH$_2$CH$_3$ ×2), 3.20 δ (3H, s,NCH$_3$), 2.45 δ (2H,m,CH$_2$CH$_2$COOEt), 2.10 δ (2H,m,CH$_2$CH$_2$COOEt), and 1.20 δ (6H,t,OCH$_2$CH$_3$ ×2). The FAB mass spectrum showed a molecular ion peak at m/z 526. This peak confirmed that the molecular weight of this compound was 526. Elemental analysis of 4,7-diamino-N-10 methylpteroylglutamate confirmed a chemical structure corresponding to C$_{24}$H$_{31}$N$_9$O$_5$.H$_2$O.

The diethyl ester of 7-aminomethotrexate (1.05 gm, 2.0 mmole) was dissolved in 50 ml ethanol. To the solution was added 2.5 ml 2N NaOH, and the solution was stirred at room temperature for 24 hours. The precipitate formed was collected and washed with ethanol. The solid was then redissolved in 50 ml water and filtered. After the filtrate had been acidified with glacial acetic acid to a pH of about 3–4, it was stored in the refrigerator overnight. The yellow crystals which formed were filtered and washed with water. After drying in vacuum, 0.9 g, corresponding to a 97% yield, of 7-aminomethotrexate, 8a was produced. This compound had a melting point of 240°–242° C. The IR spectrum (KBr) showed absorption signals corresponding to NH$_2$ at 3157.4–3438.9 cm$^{-1}$ and —C(=O). at 1636.1 cm$^{-1}$. The nmr spectrum (DMSO-d6) revealed signals at 8.20 δ (1H, d,CONH), 8.0 δ (2H,b,NH$_2$) 7.70 δ (2H,d,arom), 7.60 δ (2H,s,NH$_2$), 7.00 δ (2H,b,NH$_2$), 6.80 δ (2H,d,arom), 4.65 δ (2H,s,CH$_2$N), 4.35 δ (1H,m,NHCH), 3.20 δ (3H, s,NCH$_3$), 2.40 δ (2H,m,CH$_2$), and 2.00 δ (2H,m, CH$_2$). The FAB mass spectrum showed a molecular ion peak at m/z 468. This peak confirmed that the molecular weight of this compound was 468. Elemental analysis confirmed a chemical structure corresponding to C$_{20}$H$_{23}$N$_9$O$_5$.1.5 H$_2$O.

Synthesis of 4-amino-7-methylamino-N-10-methylpteroylglutamic acid (8b)

Procedures similar to those described above for the synthesis of compound 8a were used to prepare compound 8b from 7b, which was condensed with the diethyl L-glutamate. This condensation produced yellow prisms as the diethyl ester of 8b in a 50% yield. The melting point of this compound was 118°–120° C. The IR spectrum (KBr) showed absorption signals corresponding to $NH_2$ at 3215.5–3478.8 $cm^{-1}$, aliphatic —CH at 2974.5 $cm^{-1}$, —C(=O)— at 1731.7 $cm^{-1}$, and —C=N— at 1616.6 $cm^{-1}$. Hydrolysis by an aqueous ethanolic NaOH (90 vol. % ethanol+10 vol. % 1N aq. NaOH) gave 7-methylamino-MTX (8b). The nmr spectrum (DMSO-d6) revealed signals at 8.10 δ (1H,d,CONH), 7.71 δ (2H,d,arom), 6.74 δ (2H,d, arom), 7.35 δ (1H,d,NHCH$_3$), 6.55 δ (2H,b,NH$_2$), 4.65 δ (2H,s,CH$_2$N), 3.16 δ (3H, s,NCH$_3$), 2.95 δ (3H,d,NHCH$_3$), 2.33 δ (2H,m, CH$_2$CH$_2$), and 2.10 δ (2H,m, CH$_2$CH$_2$). Elemental analysis confirmed a chemical structure corresponding to $C_{21}H_{25}N_9O_5$.

Example 2

To verify that MTX analogs substituted with a primary or secondary amine at the 7-position have anticancer activity that is comparable to that of MTX, screening tests were conducted to determine the IC$_{50}$ value for each amine derivative, as well as further analogs having other substitutions at the 7-position. The IC$_{50}$ value is the drug concentration which inhibits cancer cell growth by 50%.

Two suspensions of human leukemia cell lines were employed in this study. The myelogenous leukemia cell line K562 was cultured in RPMI 1640 (JRH Biosciences) containing 10% filtered fetal bovine serum (FBS; Irvine Scientific), and the lymphoblastic leukemia cell line CCRF/CEM was cultured in RPMI 1640 containing 20% FBS, 100 U/ml penicillin (GIBCO Laboratories, Grand Island, N.Y.), and 100 μg/ml streptomycin (GIBCO). Cells were maintained at 37° C. with 5% CO$_2$ in air, and were cultured using standard sterile tissue culture techniques.

Prior to toxicity studies, cells were maintained 48 hours in the absence of added inhibitor. Logarithmically growing cells were inoculated at 1×10$^4$ cells/ml in tissue culture grade Petri dishes (35×10 mm), and, following a suitable recovery period, were treated with chemical agents. Inhibitor concentrations ranging from 10$^{-12}$ to 10$^{-4}$M were added to the cultures except for a control culture, which contained no added drug. Cell counts were performed by hematometer counting during 120 hours of continuous exposure to the drugs. The IC$_{50}$ value was obtained by interpolation from graphs of percent growth inhibition plotted against drug concentration.

IC$_{50}$ values obtained using the two human cell lines for MTX, 7-NH$_2$-MTX, 7-CH$_3$NH-MTX and other MTX derivatives are presented in Table 1. The IC$_{50}$ values obtained for 7-NH$_2$-MTX were slightly greater than the IC$_{50}$ values obtained for MTX. However, 7-NH$_2$-MTX was still effective at inhibiting the growth of the leukemia cell lines, and only about 6–7 times more 7-NH$_2$-MTX as compared with MTX was required to inhibit cell growth by 50%.

Substitution of the primary amine present at the 7-position with a secondary amine resulted in a reduction in the ability to inhibit growth of the leukemia cell lines. Namely, about 25–40 times more 7-CH$_3$NH-MTX as compared with MTX was required to inhibit cell growth by 50%.

The primary amino and methylamino 7-MTX derivatives were much more effective than the remaining compounds set forth in Table 1 at inhibiting cancer cell growth. For instance, halogen substitution (i.e., F or Cl) at the 7-position of MTX substantially retarded the ability to inhibit growth of leukemic cell lines, as did alkoxy (i.e., —OCH$_3$—, —OC$_2$H$_5$—, —OCH(CH$_3$)$_2$—) substitution, substitution with —N$_3$—, and substitution with various phosphorus-containing moieties (i.e., —P(O)(OH)$_2$—, —O(OCH$_3$)$_2$— and —P(OC$_2$H$_5$)$_2$—).

TABLE 1

Anticancer activity of derivatives of MTX having various substitutions at the 7-position as compared with MTX

| Compounds | IC$_{50}$ (nM) K562 Cells | CCRF/CEM Cells |
|---|---|---|
| MTX | 8 | 11 |
| 7-NH$_2$-MTX | 50 | 76 |
| 7-CH$_3$NH-MTX | 300 | 300 |
| 7-NHCH(CH$_3$)$_2$-MTX | 500 | 5000 |
| 7-N$_3$-MTX | 1000 | 2000 |
| 7-OCH$_3$-MTX | 450 | 4500 |
| 7-OC$_2$H$_5$-MTX | 850 | 4000 |
| 7-OCH(CH$_3$)$_2$-MTX | 1000 | 6000 |
| 7-P(O)(OH)$_2$-MTX | 6000 | — |
| 7-P(OCH$_3$)$_2$-MTX | 2500 | 5000 |
| 7-P(OC$_2$H$_5$)$_2$-MTX | 700 | 1000 |
| 7-F-MTX | 850 | 5000 |
| 7-Cl-MTX | 10000 | 10000 |

Example 3

The ability of 7-MTX analogs to inhibit DHFR isolated from chicken liver and L. casei were investigated and compared with the ability of MTX to inhibit DHFR. Tests were conducted to determine the ID$_{50}$ value for methotrexate analogs of the present invention. The ID$_{50}$ value is the drug concentration which inhibits enzyme activity by 50%. The inhibition of DHFR was evaluated by means of a spectrophotometric assay using the parent drug, MTX, as a control. DHFR activity was measured as the decrease over time in absorbance at 340 nm.

For this assay, 1.0 ml of an assay solution consisting of 50 mM potassium phosphate (pH 7.0), 0.1 mM dihydrofolate, 0.1 mM NADPH, 0.02 units of DHFR from chicken liver or 0.03 units of DHFR from L. casei, and concentrations of MTX or 7-substituted MTX derivatives ranging from 10$^{-9}$ to 10$^{-6}$M were employed. DHFR was diluted prior to each experiment in 50 mM potassium phosphate buffer (pH 7.0) containing 0.1 mM NADPH and 0.1% BSA.

Inhibition studies were carried out by adding to a 1.0 ml cuvette the assay solution containing all components except dihydrofolate, and then incubating the solution for 2 minutes at room temperature. The absorbance of the solution at 340 nm was recorded immediately following the addition of dihydrofolate. The mixtures were then incubated at room temperature for 5 minutes, and the absorbance at 340 nm was again recorded. The enzyme activity was calculated as the change in absorbance at 340 nm over time, and was expressed as the percentage of activity obtained in the absence of MTX or 7-substituted MTX analog. ID$_{50}$ values were determined by interpolation from graphs of percent of inhibition plotted against drug concentration.

ID$_{50}$ values against DHFR obtained from the two different sources for each of the 7-substituted MTX analogs are presented in Table 2. As can be seen from Table 2, a slightly higher concentration (i.e., about 1.5 to 2.5 times more) of 7-NH$_2$-MTX as compared with MTX was needed to inhibit DHFR by 50%. However, 7-NH$_2$-MTX was still relatively effective as a DHFR inhibitor. Similarly, about 2 to 5 times more 7-CH$_3$NH-MTX as compared to MTX was needed to inhibit DHFR by 50%.

TABLE 2

Inhibition of DHFR by various 7-substituted MTX derivatives as compared with MTX

| Compounds | ID$_{50}$ (nM) Chicken Liver DHFR | L. casei DHFR |
|---|---|---|
| MTX | 59 | 98 |
| 7-NH$_2$-MTX | 140 | 168 |
| 7-CH$_3$NH-MTX | 300 | 200 |
| 7-NHCH(CH$_3$)$_2$-MTX | 500 | 750 |
| 7-N$_3$-MTX | 400 | 200 |
| 7-OCH$_3$-MTX | 750 | 1000 |
| 7-OC$_2$H$_5$-MTX | 2000 | 1200 |
| 7-OCH(CH$_3$)$_2$-MTX | 200 | 670 |
| 7-P(O)(OH)$_2$-MTX | 10000 | 15000 |
| 7-P(OCH$_3$)$_2$-MTX | 20000 | 30000 |
| 7-P(OC$_2$H$_5$)$_2$-MTX | 10000 | 15000 |
| 7-F-MTX | 1500 | 500 |
| 7-Cl-MTX | 20000 | 50000 |

Example 4

To confirm that the decreased rate of metabolism of 7-NH$_2$-MTX as compared with MTX is due to amine-mediated inhibition of hydroxylation at the 7-position of the pteridine ring, the metabolism of this inhibitor in rabbit liver was investigated.

For these experiments, freshly isolated liver from a New Zealand white rabbit was homogenized in 400 ml of cold buffer of pH 7.6 consisting of 10 mM Tris-HCl, 25 mM sucrose and 10 mM MgCl$_2$. The homogenate was centrifuged at 1000×g for 20 minutes at 4° C., and the resulting pellet was resuspended in about 14 ml of the same buffer. One ml of a 0.5 mg/ml solution of either MTX or 7-NH$_2$-MTX was added, and the homogenate was incubated at 37° C. in a shaking water bath. Two ml samples of the homogenate were removed at 10 minute intervals. Samples were boiled 5 minutes to denature the proteins, and then centrifuged to pelletize cell debris. To determine inhibitor and 7-OH-MTX levels, 100 μl of the supernatant was analyzed by HPLC. For HPLC analysis, a Perkin-Elmer 410 LC solvent delivery system and a 5-μm IBM ODS column (4.1×250 mm) with a Guard column were employed. The mobile phase consisted of 0.1M monobasic sodium phosphate and 0.1M Tris-HCl in methanol at a final pH of 7.6. The eluate was monitored at 315 nm with a LC 90 UV variable-wavelength detector using a flow rate of 1.5 ml/minute. Detector output was recorded and integrated by a Perkin-Elmer LCI 100 integrator.

Figure 2:
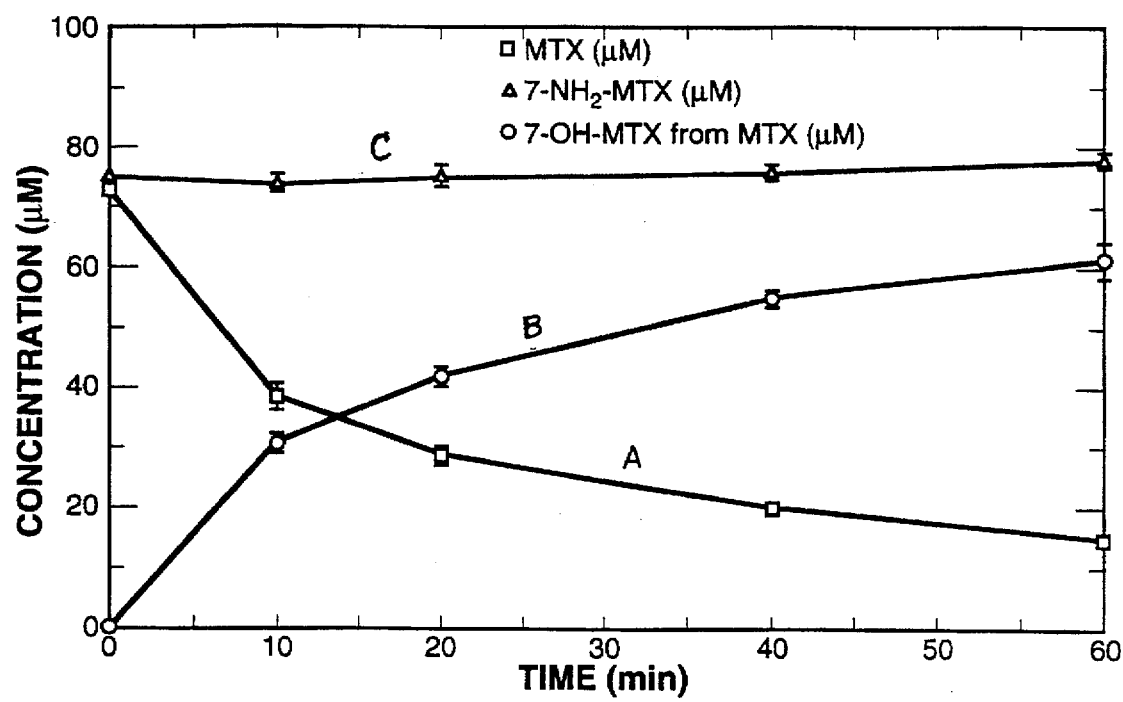
FIG. 2 depicts a graph of concentration (μM) versus time (minutes) for three different compounds. Curve A represents the concentration of the parent drug, MTX, as a function of time. Curve B represents the concentration of 7-OH MTX formed from the parent drug as a function of time. Curve C represents the concentration of 7-$NH_2$-MTX as a function of time. The data graphed is the mean±the standard error of the mean obtained from triplicate determinations.

The absence of formation of 7-OH-MTX from 7-NH$_2$-MTX as compared to that from MTX is indicated in FIG. 2. As can be seen from this figure, MTX is substantially metabolized to 7-OH-MTX within an hour, at which time less than 25% of the original concentration of MTX remains. With MTX, almost 50% of the breakdown to 7-OH-MTX occurs in the first ten minutes. In contrast, not even a slight metabolism of 7-NH$_2$-MTX to 7-OH-MTX could be detected over an hour. These results indicate that the administration of 7-NH$_2$-MTX will produce long-lived effects due to the substantial and surprising stability of this MTX analog.

All the references, including patents, patent applications, and publications, cited herein are hereby incorporated in their entireties by reference.

While this invention has been described with an emphasis upon preferred embodiments, it will be obvious to those of ordinary skill in the art that variations in the preferred compounds and methods may be used and that it is intended that the invention may be practiced otherwise than as specifically described herein. Accordingly, this invention includes all modifications encompassed within the spirit and scope of the invention as defined by the following claims.

What is claimed is:

1. A compound having the formula:

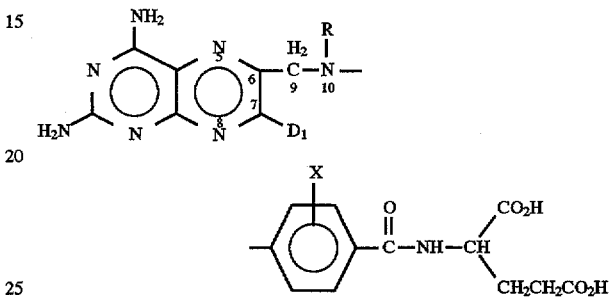

wherein R is methyl or hydro, X is halo or hydro, and D$_1$ is —NR$_1$R$_2$ wherein either both R$_1$ and R$_2$ are hydrogen, or one of R$_1$ and R$_2$ is hydrogen and the other is C$_1$–C$_2$ alkyl, C(=O)R' wherein R' is hydrogen or C$_1$–C$_2$ alkyl, or C(=O)OR" wherein R" is hydrogen or C$_1$–C$_2$ alkyl, or a therapeutically acceptable salt thereof.

2. The compound of claim 1, wherein R is methyl or hydro, X is halo or hydro, and either both R$_1$ and R$_2$ are hydrogen, or one of R$_1$ and R$_1$ is hydrogen and the other is C$_1$–C$_2$ alkyl.

3. The compound of claim 2, wherein R is methyl.

4. The compound of claim 3, wherein one of R$_1$ and R$_2$ is hydrogen and the other of R$_1$ and R$_2$ is methyl.

5. The compound of claim 2, wherein R$_1$ and R$_2$ are hydrogen.

6. The compound of claim 2, wherein X is hydro.

7. The compound of claim 6, wherein R is methyl.

8. The compound of claim 7, wherein said compound is selected from the group consisting of 4,7-diamino-N-10-methylpteroylglutamic acid and 4-amino-7-methylamino-N-10-methylpteroylglutamic acid.

9. A pharmaceutical composition comprising a pharmaceutically acceptable excipient and a therapeutically effective amount of a compound of claim 1.

10. A pharmaceutical composition comprising a pharmaceutically acceptable excipient and a therapeutically effective amount of a compound of claim 2.

11. A pharmaceutical composition comprising a pharmaceutically acceptable excipient and a therapeutically effective amount of a compound of claim 8.

12. A method of using the compound of claim 1 in treating a cancer that is capable of being treated by MTX.

13. A method of using the compound of claim 2 in treating a cancer that is capable of being treated by MTX.

14. A method of using the compound of claim 8 in treating a cancer that is capable of being treated by MTX.

* * * * *

UNITED STATES PATENT AND TRADEMARK OFFICE
CERTIFICATE OF CORRECTION

PATENT NO. : 5,698,556
DATED : December 16, 1997
INVENTOR(S) : CHAN

It is certified that error appears in the above-identified patent and that said Letters Patent is hereby corrected as shown below:

In The Specification:

In Column 1, line 24: "THF)" should read -- (THF) --.
In Column 1, line 30: "pteridinyl" should read --pteridinyl)--.
In Column 1, line 31: "glutamicacid" should read --glutamic acid--.
In Column 8, line 44: "and methylamino" should read --and 4-methylamino--.
In Column 10, lines 28 and 52, and column 11, line 19: "7-$R_1R_2$-MTX" should read --7-$NR_1R_2$-MTX--.
In Column 15, line 22: "institutes" should read --Institutes--.
In Column 15, line 40: "C-$R_5$A" should read --C-R5A--.
In Column 15, line 60: "(2)" should be inserted after "pyrazinecarbonitrile".
In Column 16, lines 9, 20, 27, 35, 36, 45, 58, and 64: The following characters should be in bold (listed respectively) 2, 2, 4, 5, 4, 5, 6, 5 (second occurrence).
In Column 16, line 19: "(4)" should be inserted after "pyrazinecarbonitrile".
In Column 17, lines 1, 16, 17, 24, 36, 38, 45, 47, 49, 51, and 60: The following characters should be in bold (listed respectively) 6, 7a, 6, 7a, 7a, 7a, 7b, 7a, and 7b, 6, 7b, 7b.
In Column 17, line 7: a space should be inserted after "6.90"
In Column 17, line 30: "e" should be --$\partial$--.
In Column 17, line 45: "pteridinylmethlyl" should read -- pteridinylmethyl--.
In Column 18, lines 2, 3, 48, 62, 64, 65, and 67: the following characters should be in bold (listed respectively) 8a, 7a, 8a, 8b, 8a and 8b, 7b, 8b.

UNITED STATES PATENT AND TRADEMARK OFFICE
CERTIFICATE OF CORRECTION

PATENT NO. : 5,698,556
DATED : December 16, 1997
INVENTOR(S) : CHAN

It is certified that error appears in the above-identified patent and that said Letters Patent is hereby corrected as shown below:

In Column 19, line 7: "8b" should read --8b--.
In Column 21, Table 2, line 15: "$_{MTX}$" should read --MTX--.
In Column 21, line 40: "S" should read --5--.
In Column 21, line 45: "a Guard" should read --a $C_{18}$ Guard --.
In Column 21, line 47: "in methanol" should read -- in 27% methanol--.

In The Claims:

In Claim 2, Column 22, line 35: "one of $R_1$ and $R_1$" should read --one of $R_1$ and $R_2$--.

Signed and Sealed this

Sixteenth Day of March, 1999

Attest:

Attesting Officer

Q. TODD DICKINSON

Acting Commissioner of Patents and Trademarks